(12) United States Patent
Stone et al.

(10) Patent No.: US 7,879,055 B1
(45) Date of Patent: Feb. 1, 2011

(54) METHOD AND APPARATUS FOR SIZING A MATERIAL

(75) Inventors: Kevin T. Stone, Winona Lake, IN (US); Troy M. Walters, Plymouth, IN (US); John J. Veca, Alta Loma, CA (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 1337 days.

(21) Appl. No.: 10/875,061

(22) Filed: Jun. 23, 2004

(51) Int. Cl.
 *A61B 17/32* (2006.01)
(52) U.S. Cl. .................................... 606/170
(58) Field of Classification Search ............... 606/170, 606/180, 184, 167, 171, 174; 600/564, 567, 600/570
See application file for complete search history.

(56) References Cited

U.S. PATENT DOCUMENTS

| | | | |
|---|---|---|---|
| 3,328,876 A | 7/1967 | Hoppe | |
| 3,372,477 A | 3/1968 | Hoppe | |
| 3,484,940 A | 12/1969 | Zell, Jr. | |
| 3,800,783 A * | 4/1974 | Jamshidi | 600/567 |
| 3,831,585 A * | 8/1974 | Brondy et al. | 600/570 |
| 3,961,419 A | 6/1976 | Schwartz | |
| 4,018,228 A * | 4/1977 | Goosen | 606/184 |
| 4,287,807 A * | 9/1981 | Pacharis et al. | 411/42 |
| 4,790,310 A * | 12/1988 | Ginsburg et al. | 606/7 |
| 5,084,058 A | 1/1992 | Li | |
| 5,133,723 A | 7/1992 | Li et al. | |
| 5,139,508 A * | 8/1992 | Kantrowitz et al. | 606/184 |
| 5,163,946 A | 11/1992 | Li | |
| 5,423,837 A | 6/1995 | Mericle et al. | |
| 5,439,470 A | 8/1995 | Li | |
| 5,477,856 A * | 12/1995 | Lundquist | 600/373 |
| 5,520,702 A | 5/1996 | Sauer et al. | |
| 5,649,939 A * | 7/1997 | Reddick | 606/148 |
| 5,746,752 A | 5/1998 | Burkhart | |
| 5,752,964 A | 5/1998 | Mericle | |
| 5,807,277 A * | 9/1998 | Swaim | 600/567 |
| 5,873,851 A * | 2/1999 | Nilsson | 604/43 |
| 5,873,876 A | 2/1999 | Christy | |
| 6,080,173 A * | 6/2000 | Williamson et al. | 606/184 |
| 6,695,859 B1 * | 2/2004 | Golden et al. | 606/184 |
| 6,733,509 B2 | 5/2004 | Nobles et al. | |
| 2004/0122450 A1 | 6/2004 | Oren et al. | |
| 2004/0210238 A1 | 10/2004 | Nobles et al. | |

* cited by examiner

*Primary Examiner*—Anhtuan T Nguyen
*Assistant Examiner*—Ryan J Severson
(74) *Attorney, Agent, or Firm*—Harness, Dickey

(57) ABSTRACT

A method and apparatus for sizing a member. The apparatus may include a first member and a second member movable relative to one another to impinge the member. The apparatus may be used in a small area to achieve a selected sizing of the member.

25 Claims, 4 Drawing Sheets

METHOD AND APPARATUS FOR SIZING A MATERIAL

FIELD

The present teachings relate generally to a method and apparatus for a surgical procedure, and particularly to a method and apparatus for positioning and sizing a flexible member relative to a portion of an anatomy.

BACKGROUND

In an anatomy, such as a human anatomy or other appropriate anatomy, various portions are generally interconnected. For example, soft tissues may be interconnected one to another and interconnected with various other portions, such as bony structures. These interconnections may be provided to allow for functioning of various features, such as muscle constrictions, tissue and organ containment, and the like. Nevertheless, due to injury, disease, fatigue, or other circumstances, various interconnections may be weakened or destroyed.

In addition, various procedures may be performed relative to an anatomy. For example, various orthopedic procedures may occur that replace or reconstruct various portions of the anatomy. To perform such procedures, soft tissue portions may be cut, resected, pierced, and may be later repaired. Various repairs may include stitching, stapling, adhering and other appropriate attachment mechanisms.

Furthermore, various procedures may include positioning an implant or prosthesis relative to a selected portion of the anatomy. The prosthesis may need to be fixed relative a selected portion of the anatomy to achieve a selected result. The prosthesis may be fixed in any appropriate manner, such as stapling, stitching, adhering or any appropriate manner.

It may be desired to achieve fixation or reconstruction of various portions of a prosthesis in the anatomy with substantially minimal or small invasion. For example, it may be desirable to position a flexible strand relative to a portion of the anatomy and remove excess portions of the flexible strand with minimal additional trauma to the anatomy. In addition, the working area within an anatomy may be substantially minimal and it may be desirable to size a fixing member substantially internally.

SUMMARY

A method and apparatus to fix or selectively size a surgical portion. For example, a flexible member, such as suture, strand, or other appropriate flexible member, may be used to fix a selected portion of or member relative to an anatomy. The flexible strand may be knotted or otherwise stitched in a selected area and the flexible strand may be sized within the anatomy. A knot may be formed in a flexible strand, such as relative to two ends of a flexible strand, and the two ends of the flexible strand may be sized. Sizing may include removing a portion of the flexible strand, to achieve selected results. An apparatus may be provided to efficiently and successfully remove extraneous portions of a flexible strand by impinging the flexible strand on a cutting portion of an apparatus. Therefore, an apparatus may include a first member and a second member. According to various embodiments, a first member may be slidable within a second member to impinge the flexible strand to size the flexible strand. A method may include the use of the apparatus and a method of using the apparatus in a selected procedure.

According to various embodiments an apparatus may be provided to size a material. The apparatus may include a first member including an inner wall defining a bore and a second member operable to be placed in the bore defined by the inner wall. A cutting area may be defined by at least a first portion of the first member or a first portion of the second member. Also, at least one of the first member or the second member may be operable to move relative to the other of the first member or the second member. The first portion of the first member and the first portion of the second member may form an interference upon an actuation of at least one of the first member or the second member.

According to various embodiments an apparatus may be provided to size a material. The apparatus may include a first member including an inner wall defining a bore and a second member operable to move relative to the inner wall. A cutting portion may be defined by the second member and an interference wall may be defined by a portion of the inner wall. The cutting portion may engage a portion of the interference wall for selected purposes, such as forming a sizing or cutting force.

According to various embodiments an apparatus for sizing a material is taught. The apparatus may include a first member including an inner wall defining a bore and a second member operable to move relative to the inner wall. A cutting portion may be defined by the first member and an interference portion may be defined by a portion of the second member. The cutting portion may engage a portion of the interference portion.

According to various embodiments a method of using an apparatus including a first member defining a bore and a second member operable to move relative to the bore to sever a third member may be taught. The method may include positioning the third member relative to at least one of the first member or the second member. The third member may be engaged with a cutting portion of at least one of the first member or the second member. According to various embodiments at least one of the first member or the second member may be moved relative to the other of the first member or the second member. An interference may be formed between the first member and the second member to engage the third member at a selected region.

BRIEF DESCRIPTION OF THE DRAWINGS

The present description and appended claims will become more fully understood from the detailed description and the accompanying drawings, wherein:

DETAILED DESCRIPTION OF VARIOUS EMBODIMENTS

The following description of various embodiments is merely exemplary in nature and is in no way intended to limit the teachings, its application, or uses.

Figure 1A:
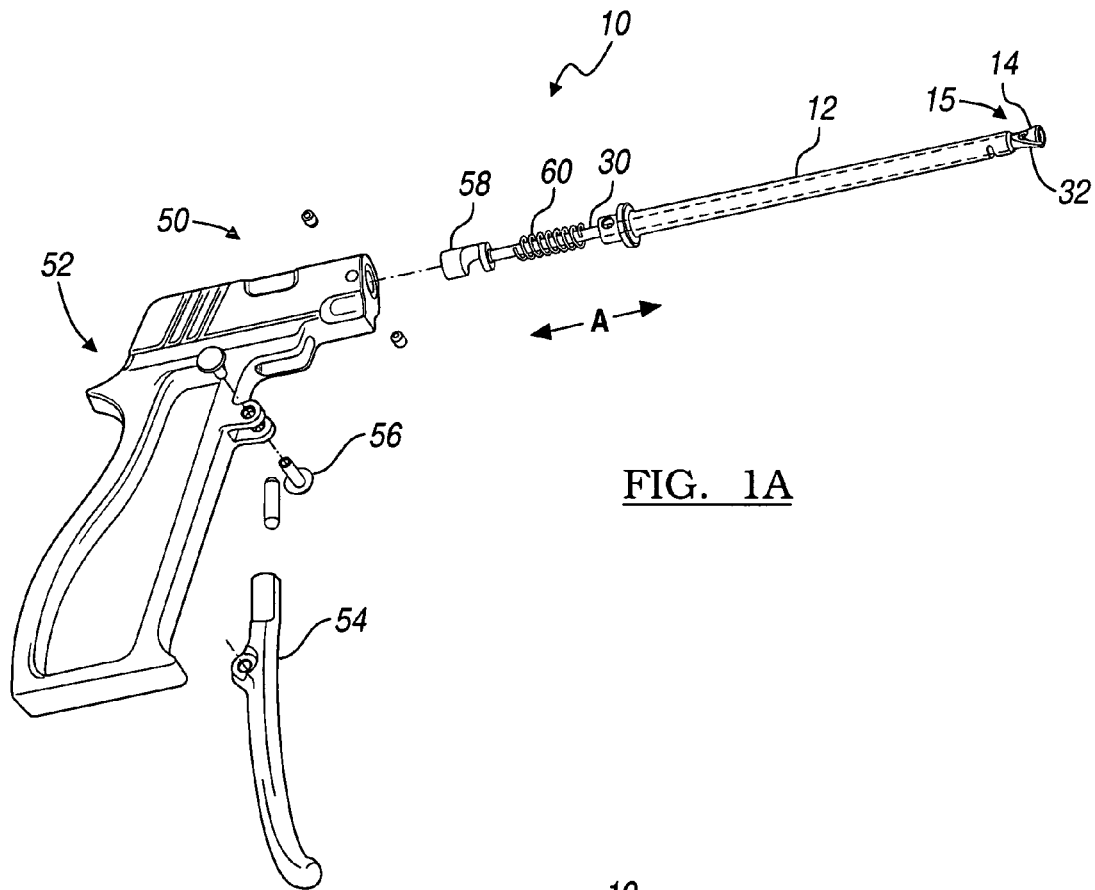
FIG. 1A is an exploded perspective view of an apparatus according to various embodiments.
Figure 1B:
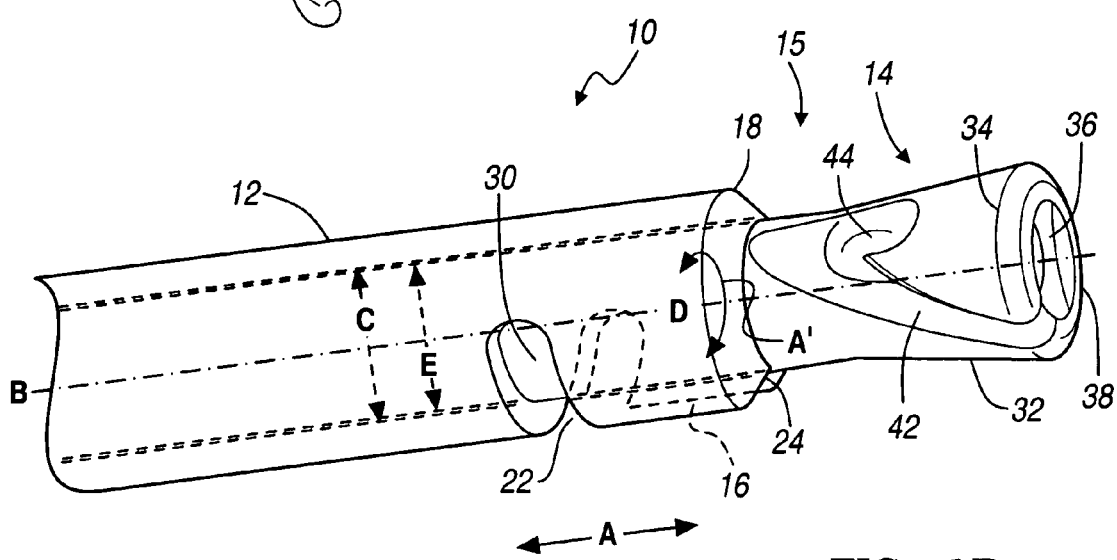
FIG. 1B is a detailed view about circle 1B of FIG. 1A.

With reference to FIGS. 1A and 1B, according a various embodiments apparatus 10 may be provided to cut a selected member. For example, the apparatus 10 may be a suture cutter operable to cut a suture that may also operate to move a knot. Nevertheless, the apparatus 10 may be used to cut any appropriate member, such as an appropriate flexible member, an appropriate non-flexible member, or any appropriate member. The apparatus 10 may generally include a first member 12, which may be an external member or sleeve. The apparatus 10 may further include a second member 14, which may be a plunger or internal portion. The first member 12 and the second member 14 may move relative to one another generally in the direction of arrow A and defining a cutting area or portion 15. That is, the sleeve 12 or the plunger 14 may be moved substantially toward or away from one another, as described herein. Moreover, the plunger 14 may be operable to slide at least a distance within the sleeve 12. Also the plunger 14 may rotate in the direction of arrow A' relative to the sleeve 12. Thus the plunger 14 may move in more than one direction relative to the sleeve 12.

The sleeve 12 may be provided along an axis B and may define a cylinder or other appropriate geometric shape having a selected internal dimension C. The tube 12 may include a bore extending through its entire length or only a portion of its length. The bore may include any appropriate dimension, shape, geometry, size, etc. The internal dimension C may be any appropriate dimension, such as a diameter of a cylinder defined by the sleeve 12. The sleeve 12 may be included in any appropriate length for selected purposes. Also the sleeve 12 and/or the bore may include any appropriate geometry, shape (such as square, rectangle, hexagon, etc.), size, or other feature. The shape, size, geometry, and other features may be altered or differ according to various embodiments.

The sleeve 12 may be formed of a substantially rigid material, such as a metal, a polymer, or any appropriate material. The sleeve 12 may be provided with a slot or passage 16 that may extend from a first end 18 of the sleeve toward a second end 20 of the sleeve. The slot 16 may extend only a distance between the first end 18 and the second end 20 or may extend substantially the entire distance along the length of the sleeve 12. Augment or secondary slots, such as a slot 22, may be provided that extends from a portion of the first slot 16 and substantially perpendicular thereto. Nevertheless, one or a plurality of slots 16, 22 may be provided in the sleeve 12 for appropriate purposes. It will be understood that the slot 16, 22 may be provided for entry and exit from the sleeve 12 of various portions and may be provided for ease of use.

The first end 18 may also define a selected portion. For example, a cutting edge 24 may be provided or formed into the first end 18. The cutting edge 24 may include a substantially beveled or sharpened portion defined by at least a portion of the first end 18 of the sleeve 12. The cutting portion 24 may engage a selected member, such as a flexible strand, to sever a portion of the flexible strand from another portion thereof. The cutting portion 24 may be provided in any appropriate manner and may be substantially smooth, serrated, or the like. Generally, the cutting edge 24 may be provided in any appropriate manner that is operable to sever a selected member at an area near the cutting edge 24.

The second member or plunger 14 may be provided to operate with the sleeve 12 in a selected manner. The plunger 14 may include a first portion or body 30 that extends a length along an axis D. The axis D may be substantially aligned with the axis B of the sleeve 12 for selected purposes, such as an appropriate use of the apparatus 10. Nevertheless, the body 30 of the plunger 14 may include any appropriate geometry or shape, such as hexagon, square, cylindrical, or size depending upon a selected application. For example, the body 30 may include a dimension E that is substantially equivalent to the dimension C of the sleeve 12. The dimension E may be smaller than the dimension C such that the plunger 14 may slide within the sleeve 12 in the direction of arrows A and/or A'. In this manner, the plunger 14 may move relative to the sleeve 12 while being held in a substantially selected orientation relative to the sleeve 12. In addition, the body 30 of the plunger 14 may be formed substantially complimentary to the sleeve 12.

Extending from the body 30 is a second portion 32. The second or expanded portion 32 of the plunger 14 may generally be an expanded portion 32. The expanded portion 32 may also be defined by any appropriate shape, size, or the like. For example, the second portion 32 may define a conical portion including a virtual apex defined within the body 30. The second portion 32 may extend outwardly from the axis D beyond the dimension E of the body 30. The second portion 32 may include any appropriate dimension that may be greater than the dimension C of the sleeve 12. In this way, as the plunger 14 moves relative to the sleeve 12, the second portion 32 may engage the first end 18 of the sleeve 12 and the cutting portion 24, as described herein.

The second portion 32 may include any appropriate features as selected. For example, a proximal end or a first end 34 of the plunger 14 may include a depression or recess 36. The recess 36 may include a central or internal portion that includes a distance below an outer or external edge 38. The depression 36 may be provided in any appropriate dimension or shape to be defined by the second portion 32.

In addition, various other features, such a slot 42, may be defined by the plunger 14. The slot 42 may be defined by either one or both of the second portion 32 and the body 30. The slot 42 may define a recess such that the slot 42 may receive a selected member such that the member does not extend beyond a dimension of the expanded portion 32 or the body 30. Also a flat or angled portion may be formed relative to or in the lot 42 to assist in positioning a member, such as a flexible member, within the slot 42. Therefore, a member may be received in the slot 42 and be held within the slot 42 without interfering with the dimension of the plunger 14. The slot 42 may also be a selected length, such as about 1 mm to about 10 cm.

Furthermore, the plunger 14 may include other features, such as a bore 44, that may be defined in either one or both of the body 30 or the expanded portion 32. The bore 44 may cooperate with the slot 42 or provided separate from the slot 42. The bore 44 may assist in operation of the apparatus as discussed herein.

Regardless, various features or architectures of the plunger 14 may be provided for various purposes, such as those described herein. The various features may assist in operation of the apparatus 10 and may be provided for any appropriate reasons. In addition, the apparatus 10 that may include cutting portions or areas 15 including the cutting edge 24 and the second portion 34 of the plunger 14. These cutting portions may be a part of a handheld or operated device or apparatus 10. The hand held apparatus 10 may include generally or substantially these portions and may be interconnected with a hand grip or actuating mechanism 50. It will be understood, however, that the apparatus 10 may be actuated in any appropriate manner.

The actuating mechanism 50 may be used to operate the cutting portion 15, including the interaction of the expanded section 32 and the cutter edge 24. The actuating mechanism 50 may operate in a generally known manner, and therefore is not to be explained in detail herein, but described briefly for reference. The actuating mechanism 50 may include a first or handle portion 52 that may be grasped by a user. A second handle or trigger portion 54 may be provided to interconnect with the first handle portion 52 in a selected manner, such as a rotating manner. The trigger mechanism 54 may ride on or move about a cylinder 56 to allow the trigger portion 54 to rotate relative to the handle 52 when actuated.

The trigger mechanism 54 may be interconnected with the body 30 at a connection region 58. The connection region 58 may interconnect with the trigger portion 54 substantially directly or through a selected linkage. The interconnection portion 58, including any selected linkages, may operate to move the body 30 in the direction of arrows A and/or A', as discussed above, at a selected time. Also the handle may be associated with or operate other portions or designs to move the parts of the apparatus 10 in any appropriate manner. The trigger 54 may actuate the apparatus 10 to perform a function or motion.

It will be understood that the trigger mechanism 54 may be interconnected with the body 30 in a selected manner such that actuation of the trigger 54 may move the plunger 14 substantially distally from the handle section 52 or proximally toward the handle portion 52. Various mechanisms may be provided, as understood by one skilled in the art, to provide the proper directional control. In addition, a return or biasing portion, such as a spring 60, may be provided to assist in forming a resting or standard position for the apparatus 10. The outer tube 12 may be interconnected with the handle portion 52 in a selected manner such that the handle portion 52 is substantially immovable or fixed relative to the outer tube 12. Nevertheless, it will be understood that the outer tube 12 may also move relative to the plunger 14. Thus the actuation may move either or both of the outer tube and/or the plunger 14.

The apparatus 10, therefore, can be provided as a substantially small instrument or as a larger instrument including a selected size of the tube 12 for a minimally or small invasive procedure. Also, the tube 12, as part of the apparatus 10, may be provided in any appropriate length. For example, the tube 12 may be provided substantially alone and include a length of about 2 to 4 cm. In addition, the tube 12 may be provided in a selected mechanism, such as with the handle portion 50, and include a length of any appropriate length such as more than about 4 cm. The extended reach of the tube portion 12 may assist in positioning a selected portion of a flexible member, such as a suture, in a selected region of an anatomy that is efficiently reachable with the tube 12. As described herein, the apparatus 10 may be used as a knot pusher in addition to a flexible member cutter. Therefore, the apparatus 10 may be provided for various purposes as further described herein.

According to various embodiments, the expanded portion 32 of the plunger 14 may move toward the cutting edge 24 defined by the tube 12. Therefore, the expanded portion 32 will be understood to move proximally toward the handle portion 50 of the apparatus 10. As discussed above, the trigger portion 54 may be provided to move the body 30 in an axial direction toward the handle 50 to actuate or move the expanded portion 32, such as by moving the body 30. As discussed herein, this interaction may provide a cutting force relative to a selected portion of the expanded portion 32. Nevertheless, the handle mechanism 50 may also provide a mechanism to move the body 30 axially away from or distal to the handle portion 50, as described herein.

Figure 2A:
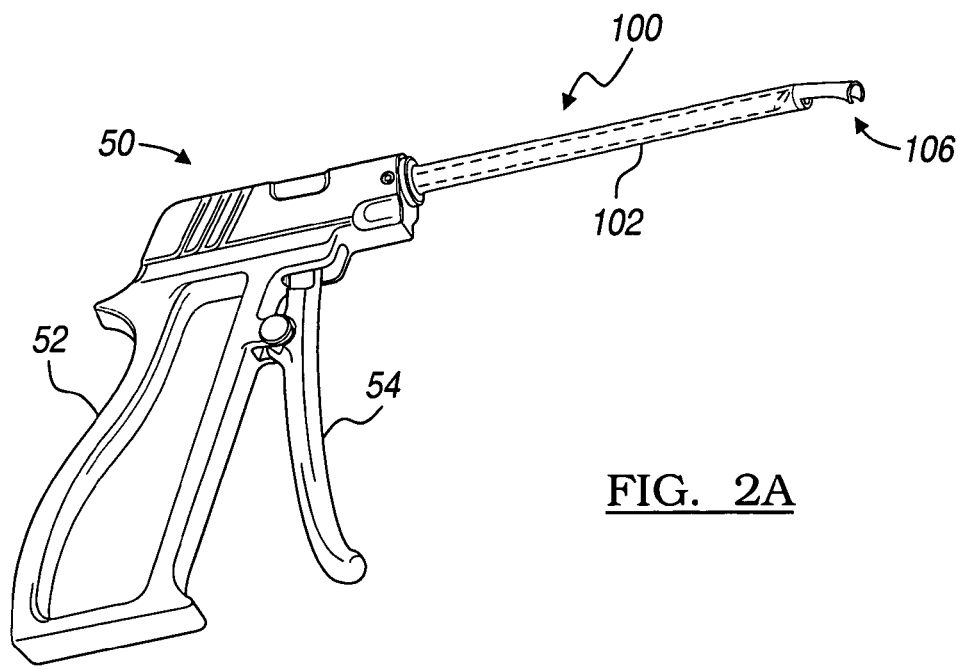
FIG. 2A is a perspective view of an apparatus according to various embodiments.
Figure 2B:
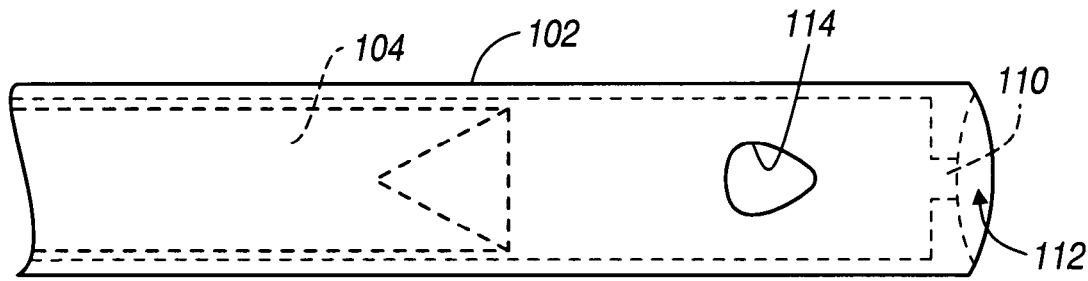
FIG. 2B is a top plan view of detail 2B from FIG. 2A.
Figure 2C:
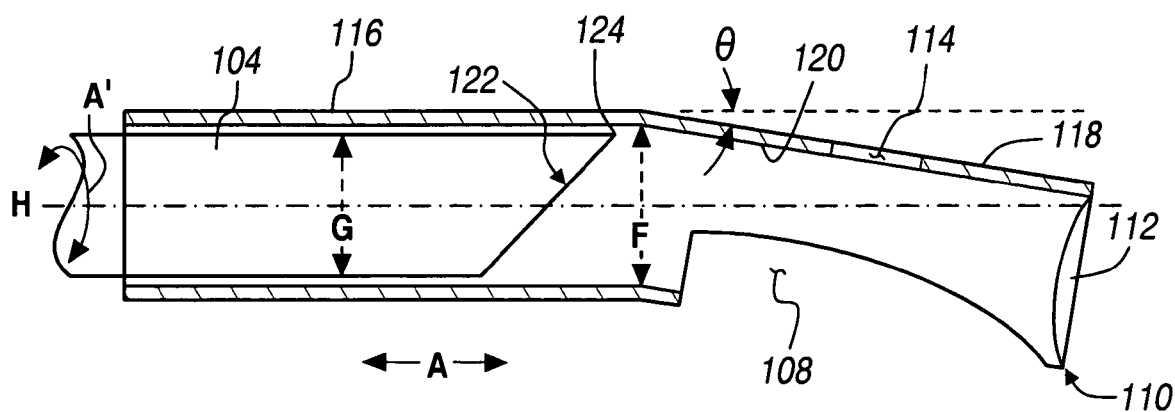
FIG. 2C is a partial cross-sectional view of detail 2C from FIG. 2A.

With reference to FIGS. 2A-2C, an apparatus 100 according to various embodiments is illustrated. The portions of the apparatus 100 similar to the portions of the apparatus 10 are referenced with similar reference numerals to the apparatus 10 and will not be re-described here below. The apparatus 100 may include a handle portion 50 similar to the handle portion 50 described above. The handle portion 50 may include a grippable portion 52 and a trigger portion 54. As described above, the trigger portion 54 may be moved relative to the gripable portion 52 to actuate a portion of the apparatus 100.

The apparatus 100 further includes an exterior or outer tube 102 and an actuating or inner tube 104. The outer tube 102 may be substantially hollow such that the inner tube 104 is operable or able to move within the outer tube 102. The inner tube 102 may be hollow or include an internal structure therein to provide a selected rigidity to the inner tube 104. Therefore, the inner tube 104 may be hollow, solid, porous or any other appropriate construction, It will be further understood that the outer tube 102 may also move relative to the inner tube 104, or both may move relative to one another.

The outer tube 102 may include a selected internal dimension F. The internal dimension F may be any appropriate dimension. Also, the outer tube 102 may include any appropriate geometry, shape, size, or the like. For example, the inner dimension F may be a diameter of a cylinder defined by the outer tube 102. The inner tube 104 may also include a selected dimension G which may be complimentary to the dimension F of the outer tube 102. The inner tube 104 may also include a shape, size, geometry or the like that may be complimentary to the interior shape of the tube 102. Therefore, the inner tube 104, for example, may generally define a cylinder where the dimension G is of a dimension that is substantially a diameter of the cylinder defined by the tube 104 and allows for the inner tube 104 to move relative to the outer tube 102.

Near a cutting or operational area 106 of the apparatus 100, a bore or cavity 108 may be defined by the outer tube 102. The cavity 108 may allow for introducing a selected member, or portion thereof, relative to the apparatus 100, such as a flexible member. Further, the outer tube 102 may define a distal or end slot 110. The slot 110 may also assist in positioning a selected member relative to the tube 102. Near the slot 110 may be a dished area or depression portion 112. The depression 112 may allow for operating or positioning a selected portion, such as a knot in a flexible member or suture, according to various embodiments. Further defined by the outer tube 102 is a bore or opening 114. The bore 114 is operable to assist in positioning and selecting a dimension formed by the apparatus 100.

The outer tube 102 may extend generally along an axis H to which an exterior wall 116 of the tube 102 may be substantially parallel. Nevertheless, a portion of the tube 102, generally near the cutting area 106 may be formed at an angle θ relative to the axis H or the proximal wall portion 116. A cutting area wall portion 118 may be provided at the angle θ to allow an interaction of the inner tube 104 with an inner wall portion 120 in the or near the cutting area 106. The angle θ may be any appropriate angle such as about 0.50 degrees to about 90 degrees. The angle θ may be selected for various purposes, such as forming a selected interference or force between the inner tube 104 and the outer tube 102 or for use of the apparatus 100. Regardless, the angle θ may be any appropriate angle according to various embodiments.

The inner tube 104 may include a cutting or engaging section 122 that may include a sharpened region 124. The sharpened region 124 may move relative to the inner wall 120 near the cutting area 106. The inner tube 104 may be formed of a resilient material that is operable to bend or move when engaging the internal wall portion 120 near the cutting area 106 such that an interference is created. As mentioned above, the selection of the angle θ may be selected depending upon the amount of interference selected between the inner tube 104 and the outer tube 102. Also, the material may also allow the inner tube 104 to return to a selected shape after the interference force is removed.

According to various embodiments, the handle mechanism 50 may be actuated to move the inner tube 104 generally in the direction of arrows A and/or A' toward the cutting area 106. Briefly, the inner tube 104 and/or the outer tube 102 may move axially and/or rotate relative to one another. As the inner tube 104 moves toward the cutting area 106, the sharpened region 124 may begin to and engage the internal wall 120 in the cutting area 106. A selected material positioned near the cutting area 106 may then be engaged with the cutting portion 124 to cut the selected material. For example, the selected material may be positioned through the bore 114 and the cutting or sharpened edge 124 may engage and sever the material upon reaching the bore 114. An area between the bore 114 and the end 110 of the outer tube 102 may be any selected distance. The distance may allow for a selected distance to be formed for a portion of the member, such as suture.

According to various embodiments, the apparatus 100 may be provided to engage a selected material, such as a flexible member, including a suture, for various purposes. The depression 112 may be used to move a knot or selected portion of the flexible member relative to another portion of the member or a selected anatomy. The cutting area 106 may be used to sever or select a length of a selected portion of the member for various purposes. Therefore, the apparatus 100 may be used to form a knotted portion of a suture or cut a suture relative to a knot in a suture, according to various embodiments.

Figure 3:
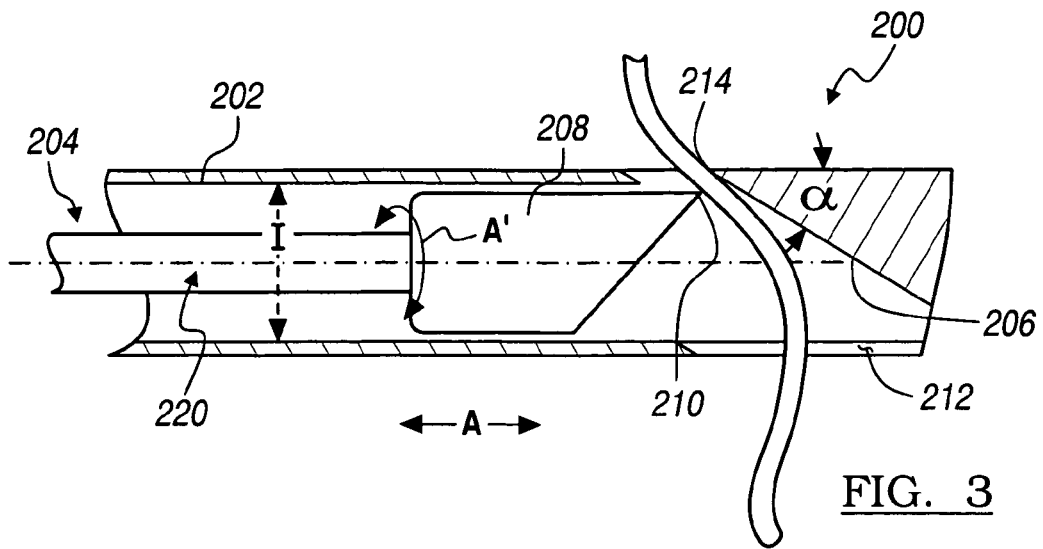
FIG. 3 is a detailed cross-sectional view of a severing area according to various embodiments.

With reference to FIG. 3, an apparatus 200 according to various embodiments is illustrated, where like reference numerals reference like portions to those described above. The apparatus 200 may include an outer tube portion or section 202 and an inner or cutting portion 204. It will be understood that the outer tube portion 202 and the inner cutting portion 204 may be interconnected with a handle portion, such as the handle portion 50. Such portions are not illustrated here for clarity. Furthermore, it will be understood that the apparatus 200 may be interconnected with any appropriate type of mechanism to allow for actuation of the apparatus 200.

The apparatus 200 may include a first dimension I, that is an internal dimension of the outer tube 202. The dimension I may be any appropriate dimension depending upon the size, shape, geometry and the like of the outer tube 202. The outer tube 202 may also define an internal edge 206 that is formed at an angle or interference dimension a relative to the remaining portions of the outer tube 202. The interference wall 206 may interact with a cutting head or portion 208 of the internal or cutting mechanism 204. A sharpened or cutting region 210 of the cutting head 208 may interact with the interference wall 206 to cut or sever a selected member, such as a flexible member or suture, when one is positioned relative to the interference wall 206.

The outer tube may define an opening or bore 212 to assist in positioning a member relative to the outer tube 202. In addition, a second bore or opening 214 may be provided to receive the member and hold it relative to the outer tube 202 for an interaction of the cutting head 208 relative to the interference wall 206. As described above, the outer tube 202 may also define a portion to assist in moving or positioning a portion of the flexible member, such as knot, in operation of the apparatus 200.

In addition, the apparatus 200, including the cutting head 208, may be moved with a resilient or flexible shaft 220. The shaft 220 may be formed of any selected material, such as nitinol to allow for a resiliently flexible material to form the shaft 220. In this manner, the cutting head 208 may be moved toward the interference wall 206 with the shaft 220, according to any appropriate mechanism. When the cutting head 208 reaches the interference wall 206, the shaft 220 may be operable to flex or bend while keeping the cutting head 208 at an interference pressure with the interference wall 206. The pressure created between the cutting edge 210 and the interference wall 206 may be dependent upon the angle α formed by the interference wall 206 and the flexibility of the shaft 220. Therefore, the amount of pressure or interference may be selected according to various purposes and based upon a selected material that is operable to be cut or formed with the apparatus 200.

Therefore, according to various embodiments, a mechanism or apparatus may be provided to perform a selected procedure. For example, an apparatus may be provided to cut a selected material, such as a flexible member, which may be used as a suture in a procedure. The apparatus may be used to position a portion defined by the member, such as knot, relative to the member or a selected portion of an anatomy. The cutter portions may be provided to exert a selected amount of force relative to a selected member.

As indicated above, various interference portions may be provided to selectively interfere with one another to form a force relative to one another. The force created may be dependent upon the amount of interference and the force applied to the interference or cutting area. Nevertheless, the amount of interference or the amount of force provided by the interference may be selected based upon selected angles, sizes, materials, and the like. Such forces may be selected and differed depending upon the material designed to be cut or severed. For example, a member formed of a substantially rigid or strong material may be cut with an apparatus including a substantially large interference. Therefore, such an apparatus may be provided to efficiently cut a selected material. Alternatively, a weaker or softer member or material may be severed with less interference.

According to various embodiments, an apparatus, such as the apparatus 10, 100, 200, may be used to sever a selected material in an anatomy. It will be understood that the apparatuses 10, 100, 200 according to various embodiments may be used for any appropriate purpose, and severing a suture or flexible member within an anatomy is merely exemplary. Nevertheless, an exemplary method of using the apparatus 10 according to various embodiments is described below. It will be understood that a similar method may be used to sever a selected material using the apparatus 100 or 200 and the description of a selected method is merely exemplary and any appropriate method may be used.

Figure 4:
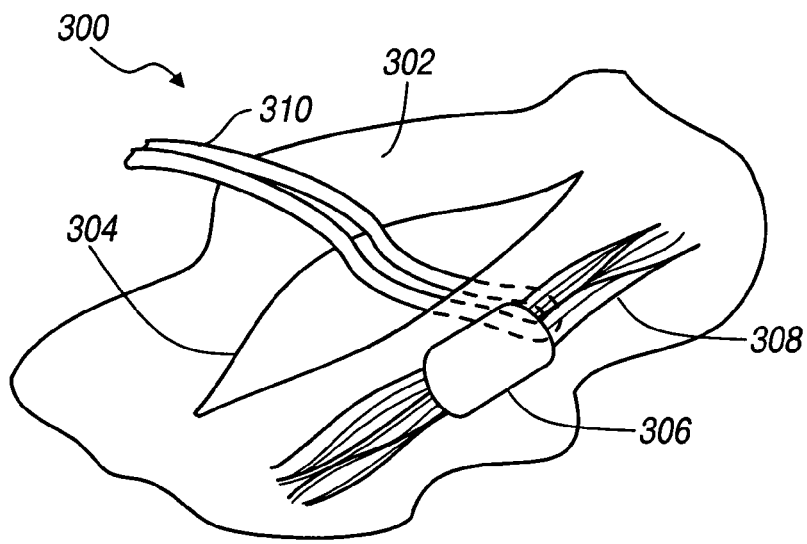
FIG. 4 is an environmental view of a portion of an anatomy.

With initial reference to FIG. 4, an anatomy 300 is exemplary illustrated. The anatomy 300 may be formed of an external soft tissue portion 302 such as skin or dermis. An incision or opening 304 may be formed in the dermis for selected purposes, such as positioning a prosthesis 306 relative to a soft tissue portion such as a muscle or tendon 308. The prosthesis 306 may be any appropriate prosthesis such as a patch or the like to allow for an interconnection of various portions of the soft tissue 308. Furthermore, it will be understood that the method may also be used for attaching two selected portions of soft tissue relative to one another, any appropriate prosthesis relative to a soft tissue or hard tissue portion, or any appropriate interconnection.

The interconnection of the prosthesis 306 to the soft tissue 308, or any appropriate interconnection, may be formed by a flexible member, such as suture 310. The suture 310 may be formed of any appropriate material, such as polyester, polyethylene, a metal, a metal alloy, any appropriate polymer, or any appropriate material. The flexible member 310 may be provided to allow for an interconnection of the prosthesis 306 with the soft tissue 308 or to form any appropriate interconnection. Nevertheless, the portion to be interconnected, such as the prosthesis 306 with the soft tissue 308, may be at a distance below or within the soft tissue dermis 302. In addition, in an attempt to reduce or minimize trauma to a patient, the incision 304 may be formed substantially minimal or small to assist in reducing or minimizing trauma to a patient. Therefore, the visualization and working area relative to the prosthesis may be substantially small.

Nevertheless, the suture 310 may be selectively knotted or fixed relative to the prosthesis 306 and the soft tissue 308. To do this, a knot 312 may be formed at an external area, an area external to the dermis 302, and pushed down a selected portion of the suture 310 to an area near the prosthesis 306. Such knot pushing or positioning methods are generally known and will not be described herein in detail, but the apparatus 10 may be provided to assist in positioning and selectively severing a portion of the suture 310.

Figure 5:
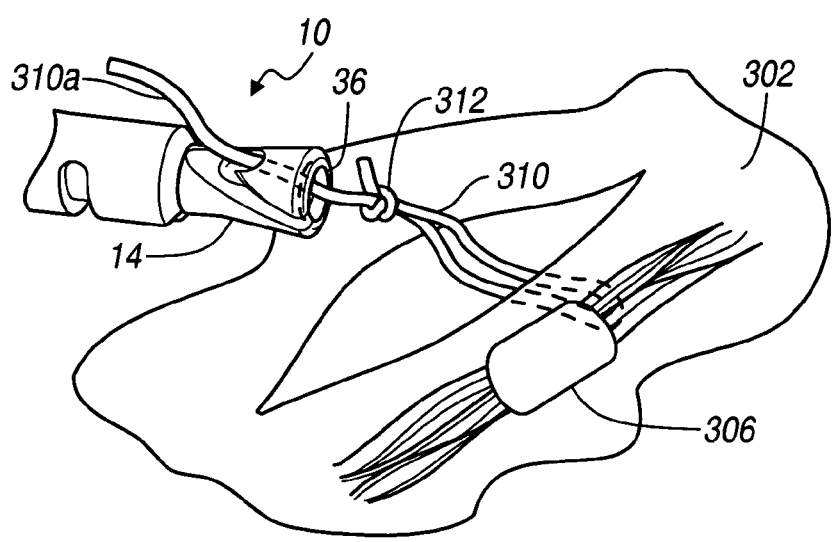
FIG. 5 is an environmental view of a the apparatus according to various embodiments.

With reference to FIG. 5, the knot 312 may be formed in the suture 310 in a selected manner. The knot 312 may also be positioned relative to the apparatus 10 in a selected manner. For example, as discussed above, the depression 36 may be formed to receive a portion or the entire portion of the knot 312. Therefore, the depression 36 may assist in positioning the knot 312 relative to a tail 310a of the suture 310. The tail 310a may also be held while the depression 36 engages the knot 312. The apparatus 10 may then be used to push the knot 312 down the tail portion 310a of the suture 310. Further, a portion of the tail 310a may be positioned in the slot 42 defined by the plunger portion 14 of the apparatus 10. Therefore, the tail 310a may be held at a position selected relative to the apparatus 10 for positioning the knot 312.

Figure 6A:
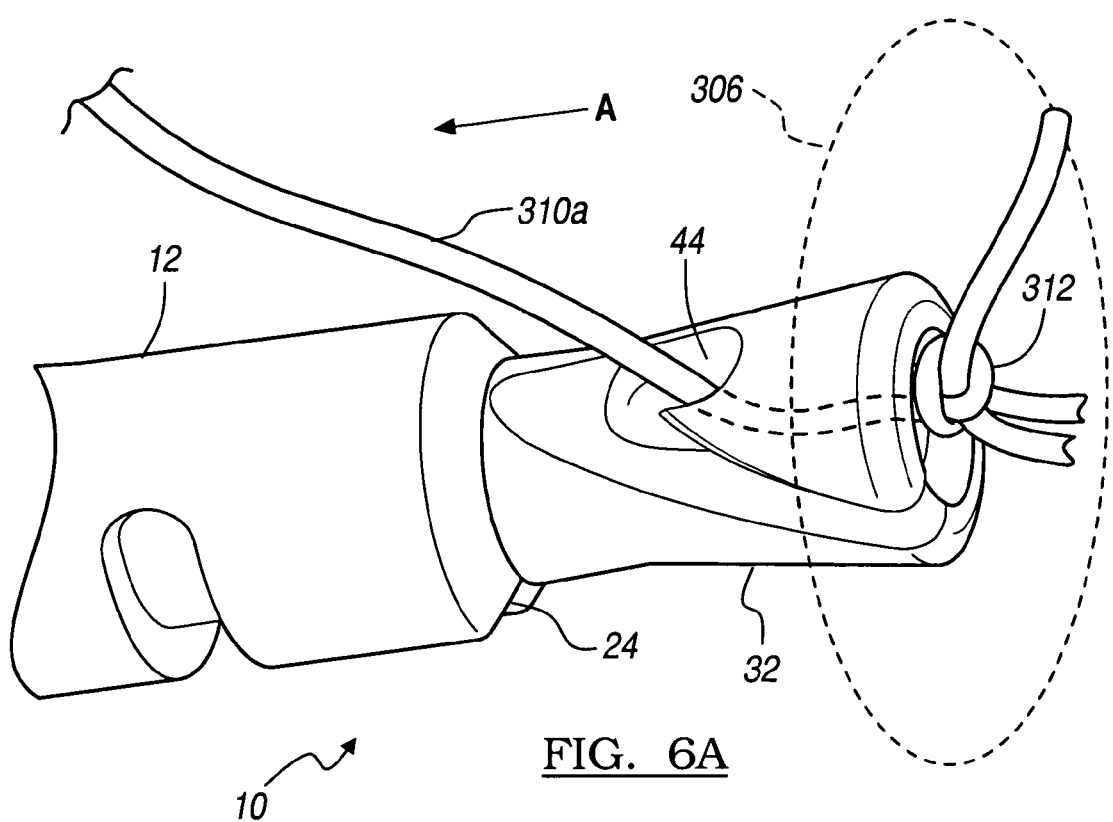
FIG. 6A is a detailed view of the apparatus according to various embodiments engaging a flexible member.
Figure 6B:
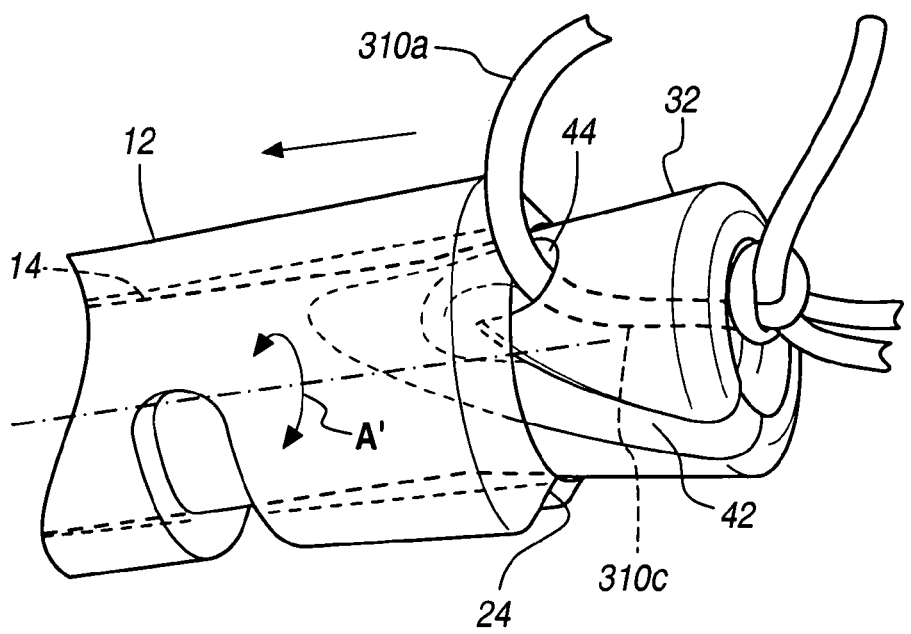
FIG. 6B is a detailed view of the apparatus according to various embodiments engaging and/or partially severing a flexible member.

With reference to FIGS. 6A and 6B, once the knot 312 is positioned relative to the prosthesis 306, the suture tail 310a may be severed or cut to a selected length. The knot 312 may be pushed to any appropriate distance from the prosthesis 306. In addition, the distal end of the plunger 14 may engage the prosthesis 306 as a reference for determining an appropriate position of the knot 312. The distal end of the plunger 14 may be provided in a substantially smooth or rounded manner such that it will not injure the prosthesis or any soft tissue through which it passes. Therefore, the plunger 14, as a portion of the apparatus 10, may be used to position the knot 312 at a selected position relative to the prosthesis 306.

Further, the tail 310a may be positioned to the slot 42 and pass through the bore 44 such that a selected portion of the tail 310a is maintained or contained within the expanded or second portion 32 of the plunger 14. This may assist in ensuring that the knot 312 is efficiently passes to a selected position relative to the prosthesis 306. Also, the portion of the suture tail 310a positioned within the slot 42 may be any appropriate or selected length, such as a portion 310c of the tail 310a which is maintained within the slot 42. The portion 310c may be any appropriate length, such as about 0.1 mm to about 10 cm.

The tail portion 310c held within the slot 42 may be any appropriate length for selected purposes. Therefore, altering the length of the slot 42 or the position of the bore 44 on the plunger 14 may alter the length of the tail 310c. Nevertheless, the slot 44 may be used to hold the suture 310, select a length of the tail 310c and assist in providing the cutting area 15.

As discussed above, the plunger 14 is operable to move in the direction of arrows A and/or A' relative to the outer tube 12. For example, upon an actuation, the plunger 14 may move toward the handle portion or toward the cutting edge 24 of the outer tube 12. Upon a deactuation or relaxing of the apparatus 10, the plunger 14 may move away from the cutting edge 24 or the handle portion 50. Also, the plunger 14 or the outer 12 may be made to rotate relative to one another, or move in any other appropriate direction. Thus the plunger 14 may move axially and/or rotate relative to the outer tube 12. Nevertheless, to cut or create the tail 310c, the plunger 14 may move toward the handle such that the expanded portion 32 of the plunger 14, operable with the bore 44, moves the suture tail 310a toward the cutting edge 24. After a selected amount of movement, the cutting edge 24 engages the suture 310a between the cutting edge 24 and a portion of the bore 44. After the application of selected amounts of force, the cutting edge 24 severs the tail 310a leaving only the tail 310c.

After the cut is made the tail 310a may be removed from the area of the knot 312. Particularly, the tail 310a may be held external from the incision 304 to assist in its removal from the anatomy 300. The apparatus 10 may then be relaxed to allow for movement of the expanding portion 32 away from the cutting edge 24. The relaxing may allow the apparatus to be removed from the anatomy 300 without impinging the suture tail 310c. The process may be repeated a number of times depending upon other knots or suture portions that need to be formed in the suture 310 or relative to the prosthesis 306.

It will be understood that the slots 16 formed in the outer tube 12 may allow for expansion of the outer tube 12 when engaged by the expanded portion 32 of the plunger 14. The slots allow the portion of the tube 12 to flex such that the tube 12 is not permanently deformed, but that the cutting edge 24 is operable to cut the suture tail 310a and relax to a selected position for further use of the apparatus 10. It will be understood that the tube 12 may be formed of selected materials to assist in this relaxing and returning to its original form as well.

Although various embodiments are described in the method illustrated in FIGS. 4-6B, it will be understood that any appropriate apparatus may be used to cut the suture in a selected manner. For example, the apparatus 100, 200 may move a plunger or internal portion substantially away from the handle portion to cut or sever a selected portion of the suture. Therefore, a selected motion or a single motion is not necessary or intended to limit the scope of the teachings.

Furthermore, as discussed above, various interferences may be formed to increase or create a selectively high amount of interference to create a great force relative to the suture tail 310a. For example, a substantially tough or strong piece of material may require a large amount of force to be applied to cut the suture material. Therefore, the size of the second portion 32 of the plunger 14 may be large relative to the dimension of the outer tube 12 to ensure that a proper interference is created. For example, the various apparatuses 10, 100, 200 may be able to create a force of about 1 Newton per mm$^2$ to about 10,000 Newtons per mm$^2$ (about 145 PSI to about 1,450,000 PSI). Therefore the apparatus 10, 100, 200 may produce a substantially large force to assist in cutting a substantially strong material. Therefore, substantially any material may be used to form the suture 310. In addition, the apparatuses 10, 100, 200, according to various embodiments, may be used to cut or size any appropriate material or member.

Selected cutting or interference forces or amounts of interference may be used for various materials of members. For example a flexible member, such as a suture, formed of one or several materials may require less force to sever than a flexible member formed of a different material. Also, compound sutures, sutures that are braided and/or formed of more than one material may require a larger cutting or interference force. Therefore, it will be understood that different materials may require different cutting forces. Also, those cutting forces may be efficiently created with apparatus according to various embodiments.

Also, as described above the apparatus, according to various embodiments, may be formed to move in a plurality of ways. The apparatus may move substantially axially, rotationally, radially, and any other appropriate motion. Moreover, various portions or members of the apparatus may move in more than one manner relative to another portion of the apparatus. Thus a cutting or interference force may be formed through, for example, both axial and radial movement of portions of the apparatus. Thus, it will be understood, that the motion of the various portions of the apparatus are not limited to a single motion.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. An apparatus, comprising:
 a first member including an inner wall defining a bore along a longitudinal central axis and a sharpened terminal end;
 a second member operable to be placed in said bore defined by said inner wall, said second member having opposing surfaces formed in an outer wall that define an open slot therebetween, said open slot having an entrance opening and an exit opening, one of said entrance and exit openings being coaxial with said longitudinal central axis, wherein said open slot extends along and through said outer wall from said entrance opening to said exit opening;
 a cutting area defined by at least a first portion of said first member including the sharpened terminal end or a first portion of said second member;
 at least one of said first member or said second member is operable to move relative to the other of said first member or said second member;
 wherein said first portion of said first member and said first portion of said second member are operable to form an interference at the cutting area upon moving at least one of said first member or said second member to cut a third member.

2. The apparatus of claim 1, wherein said first member defines said cutting area at an end of said first member.

3. The apparatus of claim 2, wherein said second member defines an interference area positionable near said cutting area.

4. The apparatus of claim 3, wherein said interference area is movable relative to said cutting area to form said interference.

5. The apparatus of claim 4, further comprising:
 an actuation mechanism;
 wherein said actuation mechanism is operable to move said second member relative to said first member to form said interference by engaging said interference area with said cutting area.

6. The apparatus of claim 5 wherein said first member defines a slot such that said first member expands radially outwardly as said interference area of said second member engages said cutting area of said first member.

7. The apparatus of claim 1, wherein said second member includes an expanded area extending from a portion of said second member operable to engage said cutting area defined by said first member.

8. The apparatus of claim 7, wherein an interference area substantially includes a conical portion defined by said second member including at least a virtual apex defined within and away from a terminal end of said second member.

9. The apparatus of claim 1, wherein said sharpened terminal end of said first member includes a cutting edge and said second member includes an interference portion;
 wherein the actuation includes movement of said first member toward the interference portion.

10. The apparatus of claim 1, further comprising:
 a length defining portion;
 wherein said length defining portion is operable with said cutting area to select a length of the third member.

11. The apparatus of claim 1 wherein said cutting area engages a portion of the third member at a first end of said open slot.

12. The apparatus of claim 11 wherein a hooked portion is located on said second member at a transition between said open slot and said first end of said open slot, said hooked portion operable to assist in positioning said third member into said open slot.

13. The apparatus of claim 11 wherein said open slot terminates at a second end of said open slot in a recess defined at a distal end of said second member.

14. The apparatus of claim 1, further comprising:
 an actuation mechanism including a handle portion and a trigger portion;
 wherein said actuation mechanism is operable to be grasped by a user to move at least one of said handle portion or said trigger portion relative to the other of said handle portion or said trigger portion to move at least one of said first member or said second member.

15. The apparatus of claim 1, wherein said first member or said second member are movable relative to the other of said first member or said second member in at least one of an axial manner, a rotational manner, a radial manner, or combinations thereof.

16. The apparatus of claim 1 wherein said opposing surfaces are fixed relative to each other.

17. An apparatus, comprising:
 a first member extending from a proximal end to a distal end and including an inner wall and an outer wall that collectively define a first bore and a second bore, the second bore being offset proximally from said distal end, said first bore communicating with a terminal end of said distal end;
 a second member having a flexible shaft and a cutting head, said second member operable to move axially relative to said inner wall;
 a cutting portion located on said cutting head; and
 an interference portion defined by a portion of said inner wall, said interference portion extending at an acute angle relative to a longitudinal axis of said first member from said second bore to said first bore, said interference portion intersecting said longitudinal axis while said outer wall maintains a cylindrical profile along an entire length of said first member;

wherein said cutting portion is operable to slidably engage a portion of said interference portion at a location distally relative to said second bore during axial movement of said second member in said first member and wherein said flexible shaft flexes to accommodate slidable movement of said cutting portion along said interference portion.

18. The apparatus of claim 17, wherein said second member is substantially solid.

19. The apparatus of claim 17, wherein said cutting portion includes a cutting edge defined by said second member;

wherein said interference portion is operable to engage said cutting edge to define said cutting portion.

20. The apparatus of claim 17, wherein said interference portion includes a distal end defining a holding area.

21. The apparatus of claim 17, further comprising:

an actuation mechanism including a first member and a second member;

wherein actuation of said actuation mechanism is operable to move at least one of said first member and said second member relative to the other of said first member and said second member.

22. The apparatus of claim 17, wherein said first member is operable to move at least one of axially, radially, linearly, rotationally, or combinations thereof relative to said second member.

23. An apparatus, comprising:

a first member defining a longitudinal central axis and including an inner wall defining a passage, said first member defining a first slot that extends parallel with said longitudinal central axis and a secondary slot that connects with said first slot and that extends substantially perpendicular to said longitudinal central axis;

a second member moveable within said passage; and a cutting region including:

an enlarged conical portion including an exterior wall defined by said second member that extends away from said longitudinal central axis;

an interference wall defined by said first member;

wherein said conical portion is operable to engage said interference wall to cut a third member and wherein said first and secondary slots cooperate to accommodate radial expansion of said first member while said first member resiliently flexes and said conical portion engages said interference wall.

24. The apparatus of claim 23, wherein the interference wall is a terminal end of said first member;

wherein said conical portion engages the interference wall of said first member on an exterior of said first member.

25. The apparatus of claim 23, further comprising:

an actuation mechanism including a handle portion and a trigger portion;

wherein at least the handle portion extends at an angle to said first member to substantially define a pistol grip;

wherein said actuation mechanism is operable to be grasped by a user to move at least one of said handle portion or said trigger portion relative to the other of said handle portion or said trigger portion to move at least one of said first member or said second member.

* * * * *

UNITED STATES PATENT AND TRADEMARK OFFICE
CERTIFICATE OF CORRECTION

PATENT NO. : 7,879,055 B1  
APPLICATION NO. : 10/875061  
DATED : February 1, 2011  
INVENTOR(S) : Stone et al.

Page 1 of 1

It is certified that error appears in the above-identified patent and that said Letters Patent is hereby corrected as shown below:

Column 1, line 33, after "relative", insert --to--.
Column 2, line 61, after "of", delete "a".
Column 3, line 7, delete "a" and replace with "to".
Column 4, line 16, delete "complimentary" and replace with "complementary".
Column 4, line 38, delete "a" and replace with "as".
Column 4, line 45, delete "lot 42" and replace with "slot 42".
Column 4, line 55, after "or", insert --be--.
Column 6, lines 19-20, delete "inner tube 102" and replace with "outer tube 102".
Column 6, line 23, delete "construction," and replace with "construction.".
Column 6, line 32, delete "complimentary" and replace with "complementary".
Column 6, line 35, delete "complimentary" and replace with "complementary".
Column 9, line 64, after "knot 312", delete "is".
Column 10, line 16, after "outer", insert --tube--.

Signed and Sealed this

Third Day of May, 2011

David J. Kappos
*Director of the United States Patent and Trademark Office*